United States Patent
Rautenberg-Groth et al.

(10) Patent No.: US 10,328,007 B2
(45) Date of Patent: Jun. 25, 2019

(54) HAIR STRAIGHTENING WITH CARBOCISTEINE

(71) Applicant: Henkel AG & Co. KGaA, Duesseldorf (DE)

(72) Inventors: Birgit Rautenberg-Groth, Ellerau (DE); Stephan Schwartz, Wedel (DE); Katharina Krause, Hamburg (DE)

(73) Assignee: Henkel AG & Co. KGaA (DE)

( * ) Notice: Subject to any disclaimer, the term of this patent is extended or adjusted under 35 U.S.C. 154(b) by 247 days.

(21) Appl. No.: 15/165,187

(22) Filed: May 26, 2016

(65) Prior Publication Data

US 2016/0263000 A1    Sep. 15, 2016

Related U.S. Application Data

(63) Continuation of application No. PCT/DE2014/200445, filed on Sep. 5, 2014.

(30) Foreign Application Priority Data

Dec. 13, 2013  (DE) .......... 10 2013 225 916

(51) Int. Cl.
| | | |
|---|---|---|
| *A61Q 5/04* | (2006.01) | |
| *A61K 8/44* | (2006.01) | |
| *A45D 2/00* | (2006.01) | |
| *A45D 2/36* | (2006.01) | |
| *A45D 7/04* | (2006.01) | |
| *A45D 7/06* | (2006.01) | |
| *A61K 8/41* | (2006.01) | |

(52) U.S. Cl.
CPC .............. *A61K 8/447* (2013.01); *A45D 2/001* (2013.01); *A45D 2/36* (2013.01); *A45D 7/04* (2013.01); *A45D 7/06* (2013.01); *A61K 8/416* (2013.01); *A61Q 5/04* (2013.01); *A61K 2800/40* (2013.01)

(58) Field of Classification Search
None
See application file for complete search history.

(56) References Cited

U.S. PATENT DOCUMENTS

| | | | | |
|---|---|---|---|---|
| 4,172,887 A | * | 10/1979 | Vanlerberghe | A61K 8/88 424/70.17 |
| 2005/0136017 A1 | * | 6/2005 | Malle | A61K 8/42 424/70.2 |
| 2012/0244082 A1 | * | 9/2012 | Sulzbach | A61K 8/046 424/47 |
| 2015/0114424 A1 | | 4/2015 | Wolff et al. | |

FOREIGN PATENT DOCUMENTS

| | | |
|---|---|---|
| DE | 102012222286 A1 | 9/2013 |
| WO | 2007/128983 A1 | 11/2007 |

OTHER PUBLICATIONS

PCT International Search Report (PCT/DE2014/200445) dated Nov. 25, 2014.

* cited by examiner

Primary Examiner — Jyothsna A Venkat
(74) Attorney, Agent, or Firm — P. Scott Smith

(57) ABSTRACT

Methods for styling, in particular for straightening, keratin fibers, in particular human hair, in which (i) a styling agent comprising carbocisteine and/or a salt thereof is applied to the keratin fibers and left there, (ii) the fibers, after a leave-in time, —are not rinsed, —are optionally dried, (iii) the fibers are mechanically deformed from exposure to heat, significantly minimize the negative consequences of styling and reduce in particular electrostatic charging and hydrophilization of the hair.

16 Claims, No Drawings

HAIR STRAIGHTENING WITH CARBOCISTEINE

FIELD OF THE INVENTION

The present invention generally relates to the technical field of styling keratin fibers, in particular human hair. The subject matter of the invention is an improved method for styling keratin fibers, in particular human hair. The keratin fibers used may in principle be all types of animal hair, for example wool, horsehair, angora hair, furs, feathers and products or textiles made therefrom. However, the invention is preferably used in the context of hair styling, in particular for straightening curly human hair and wigs made therefrom.

BACKGROUND OF THE INVENTION

A lasting deformation of keratin fibers is usually carried out in such a way that the fiber is deformed mechanically and the deformation is fixed by suitable aids. Before and/or after this deformation, the fibers are treated with a keratin-reducing preparation. After a rinsing operation, the fiber is then treated with an oxidizing agent preparation in the so-called fixing step, rinsed, and freed of the deformation aids (for example rollers, papillotes) after or during the fixing step. If a mercaptan, for example ammonium thioglycolate, is used as the keratin-reducing component, this cleaves some of the disulfide bridges of the keratin molecule to —SH groups, resulting in softening of the keratin fibers. During the subsequent oxidative fixing, disulfide bridges in the hair keratin are joined again so that the keratin structure is fixed in the predefined shape. Alternatively, instead of mercaptan, it is known to use sulfite for deforming hair. By means of hydrogen sulfite solutions and/or sulfite solutions and/or disulfite solutions, disulfide bridges of the keratin are cleaved in a sulfitolysis according to the equation

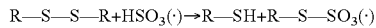

and in this way the keratin fibers are softened. Reducing agents including hydrogen sulfite, sulfite or disulfite do not have the strong odor of the agents containing mercaptan. The cleavage can be reversed, as outlined above, in a fixing step by means of an oxidizing agent to form new disulfide bridges.

The permanent straightening of keratin fibers is achieved in an analogous manner by using keratin-reducing and keratin-oxidizing compositions. In such a method, the curly hair is either wound onto rollers having a large diameter of usually more than 15 mm or the hair is combed straight under the effect of the keratin-reducing composition. Instead of the roller, it is also possible to lay the fibers straight on a straightening board. Straightening boards are usually rectangular sheets, for example made of plastic. Preferably, the fiber is wetted with the keratin-reducing preparation during this process.

A further possibility for straightening hair is straightening using hot irons. However, the structure of the keratin fiber changes during the heat treatment of the hair during the straightening operation. This change in the structure of the fiber should be counteracted by suitable measures.

Straightening by means of straightening irons can be aided by applying alkaline products beforehand. In contrast to styling by means of keratin-reducing and keratin-oxidizing compositions, such alkaline styling agents do not lead to a restructuring of the disulfide bridges but rather to a destruction of the disulfide bridges so as to form monosulfide bridges. Depending on the concentration and duration of application of the alkaline styling agents, protein chains are also hydrolytically cleaved. The pH of the alkaline styling agents is usually in the range of 11-14, preferably 12-13.

In general, the known styling methods, particularly in the case of straightening, have the disadvantage that the keratin fibers become electrostatically charged. In addition, the treatment with styling agents leads to an increased hydrophilicity of the hair, which makes it more difficult to manage and has a disadvantageous effect on hold, combability and shine.

The object of the invention is therefore to provide a styling method for keratin fibers, in particular for human hair, which delivers a very good and long-lasting styling result and at the same time minimizes the electrostatic charging and hydrophilization of the hair, cares for the fiber and is gentle on the structure of the fiber.

It has surprisingly been found that a treatment of the fibers with special styling agents prior to the styling process considerably minimizes the negative consequences of the styling and in particular minimizes the electrostatic charging and hydrophilization of the hair.

Furthermore, other desirable features and characteristics of the present invention will become apparent from the subsequent detailed description of the invention and the appended claims, taken in conjunction with this background of the invention.

BRIEF SUMMARY OF THE INVENTION

A method for styling, in particular for straightening, keratin fibers, in particular human hair, in which a styling agent comprising carbocisteine and/or a salt thereof is applied to the keratin fibers and left there; the fibers, after a leave-in time, are not rinsed, are optionally dried; and the fibers are mechanically deformed from exposure to heat.

The use of carbocisteine and/or salts thereof for protecting keratin fibers, in particular human hair, during styling methods.

The use of carbocisteine and/or salts thereof for preventing electrostatic charging and hydrophilization of keratin fibers, in particular human hair, during styling methods.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The subject matter of the present invention is, in a first embodiment, a method for styling, in particular for straightening, keratin fibers, in particular human hair, in which
(i) a styling agent comprising carbocisteine and/or a salt thereof is applied to the keratin fibers and left there,
(ii) the fibers, after a leave-in time,
    are not rinsed,
    are optionally dried,
(iii) the fibers are mechanically deformed from exposure to heat.

In the method according to the invention, first a styling agent comprising carbocisteine and/or salts thereof is applied to the keratin fibers and left there. This step (i) of the method according to the invention may take place immediately, that is to say a few seconds to minutes, before the actual styling treatment, but it is also possible to wait longer if this should be desirable in the individual case. The preferred leave-in time in step (ii) is 30 seconds to 15 minutes. Preferably, the leave-in time in step (ii) of the method according to the invention is 30 seconds to 10 minutes, more preferably 1 to 5 minutes and in particular 90 to 240 seconds.

The styling agent applied in step (i) is not rinsed out after the leave-in time but rather remains on the fiber. In step (ii), the fiber may optionally be dried, which in the case of relatively long leave-in times of the styling agent may take place by means of air drying. In the case of shorter application times, the hair may for example be rubbed with a towel or preferably blow-dried. At the end of a towel-drying step, a tangible residual moisture remains in the hair.

The fibers are then mechanically deformed in step (iii), which may take place at room temperature or also with the application of heat.

The styling agents used in the method according to the invention include carbocisteine and/or salts thereof. Carbocisteine, also known as S-carboxymethyl-L-cysteine or (R)-2-amino-4-thiaadipic acid or L-2-amino-3-(carboxymethyl-thio)propionic acid, is described by the formula

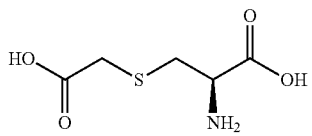

Suitable salts are in particular the mono- and di-alkali metal salts, in particular monosodium carbocysteinate, disodium carbocysteinate, monopotassium carbocysteinate and dipotassium carbocysteinate.

Methods which are preferred according to the invention are characterized in that, in step (i), a styling agent is applied which includes, based on its weight, 0.01 to 10 wt. %, preferably 0.1 to 7.5 wt. %, more preferably 0.25 to 5 wt. %, even more preferably 0.5 to 2.5 wt. % and in particular 0.55 to 2 wt. % carbocisteine.

The styling agents used in the method according to the invention are preferably water-based. More preferably, they include water in amounts greater than 25 wt. %, in each case based on the total weight of the styling agent, methods which are preferred according to the invention being characterized in that, in step (i), a styling agent is applied which includes, based on its weight, 30 to 95 wt. %, preferably 40 to 92.5 wt. %, more preferably 50 to 90 wt. %, even more preferably 60 to 87.5 wt. % and in particular 70 to 85 wt. % water.

The styling agents used in the method according to the invention may include further ingredients, wherein the use of fatty substance(s) and cationic compounds has proven to be particularly suitable.

With particular preference, the styling agents used in the method according to the invention include fatty substances (Fats) as a further active ingredient, Fats are to be understood to mean fatty acids, fatty alcohols, natural and synthetic waxes, which may be both in solid form and liquid in aqueous dispersion, and natural and synthetic cosmetic oil components.

As fatty acids (Fatacs), use may be made of linear and/or branched, saturated and/or unsaturated fatty acids having 6-30 carbon atoms. Preference is given to fatty acids having 10-22 carbon atoms. Among these, mention may be made for example of the isostearic acids, such as the commercial products Emersol® 871 and Emersol® 875, and isopalmitic acids, such as the commercial product Edenor® IP 95, and also all other fatty acids sold under the trade names Edenor® (Cognis). Other typical examples of such fatty acids are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid and erucic acid, as well as the technical mixtures thereof. Particular preference is usually given to the fatty acid fractions obtainable from coconut oil or palm oil; the use of stearic acid is generally particularly preferred.

The use amount is 0.1-15 wt. %, based on the total agent. The amount is preferably 0.5-10 wt. %, and amounts of 1-5 wt. % may be very particularly advantageous.

As fatty alcohols (Fatals), use may be made of saturated, mono- or polyunsaturated, branched or unbranched fatty alcohols having $C_6$-$C_{30}$, preferably $C_{10}$-$C_{22}$ and very particularly preferably $C_{12}$-$C_{22}$ carbon atoms. In the context of the invention, use may be made for example of decanol, octanol, octenol, dodecenol, decenol, octadienol, dodecadienol, decadienol, oleyl alcohol, erucic alcohol, ricinoleic alcohol, stearyl alcohol, isostearyl alcohol, cetyl alcohol, lauryl alcohol, myristyl alcohol, arachidyl alcohol, caprylic alcohol, capric alcohol, linoleyl alcohol, linolenyl alcohol and behenyl alcohol, and Guerbet alcohols thereof, this list being intended to be of exemplary and non-limiting nature. However, the fatty alcohols originate from preferably natural fatty acids, it usually being possible to start from an isolation from the esters of the fatty acids by reduction. Those fatty alcohol fractions which are a mixture of different fatty alcohols can also be used according to the invention. Such substances can be purchased for example under the trade names Stenol®, for example Stenol® 1618, or Lanette®, for example Lanette® O, or Lorol®, for example Lorol® C8, Lorol® C14, Lorol® C18, Lorol® C8-18, HD-Ocenol®, Crodacol®, for example Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24.

Of course, wool wax alcohols such as those which can be purchased under the trade names Corona®, White Swan®, Coronet® or Fluilan®, can also be used according to the invention. The fatty alcohols are used in amounts of 0.1-30 wt. %, based on the total preparation, preferably in amounts of 0.1-20 wt. %.

Natural or synthetic waxes (Fatwaxes) which can be used according to the invention are solid paraffins or isoparaffins, carnauba wax, beeswax, candelilla wax, ozokerite, ceresin, spermaceti, sunflower wax, fruit waxes such as apple wax or citrus wax for example, and microwaxes of PE or PP. Such waxes are available for example from the company Kahl & Co., Trittau.

The use amount is 0.1 to 50 wt. %, based on the total agent, preferably 0.1 to 20 wt. % and particularly preferably 0.1 to 15 wt. %, based on the total agent.

The total amount of oil and fat components in the styling agents used in the method according to the invention is usually 0.5-75 wt. %, based on the total agent. Amounts of 0.5-35 wt. % are preferred according to the invention.

Preferred fatty substances are linear and branched, saturated and unsaturated fatty alcohols or natural fatty alcohol mixtures having 8 to 22 carbon atoms in the alkyl chain, such as for example decanol, octanol, octenol, dodecenol, decenol, octadienol, dodecadienol, decadienol, oleyl alcohol, erucic alcohol, ricinoleic alcohol, stearyl alcohol, isostearyl alcohol, cetyl alcohol, lauryl alcohol, myristyl alcohol, arachidyl alcohol, caprylic alcohol, capric alcohol, linoleyl alcohol, linolenyl alcohol and behenyl alcohol, and Guerbet alcohols thereof, as well as fatty alcohol fractions which are produced by reducing naturally occurring triglycerides such as beef tallow, palm oil, peanut oil, rapeseed oil, cottonseed oil, soybean oil, sunflower oil and linseed oil, or fatty acid esters produced from the transesterification products thereof with suitable alcohols. The fatty alcohols are usually used in amounts of 0.01 to 15 wt. %, preferably 0.1 to 10 wt. % and particularly preferably 0.3 to 6 wt. %, based on the total preparation.

As fatty substances, use may also be made of monoesters of fatty acids with alcohols having 6 to 24 C atoms, and also triglycerides of natural origin.

Methods which are particularly preferred according to the invention are characterized in that, in step (i), a styling agent is applied which includes, based on its weight, 0.15 to 7.5 wt. %, preferably 0.15 to 5 wt. %, more preferably 0.2 to 4 wt. %, even more preferably 0.25 to 3 wt. % and in particular 0.3 to 1 wt. % quaternary ammonium compound(s) of the group
  i) tetraalkylammonium halides and/or
  ii) esterquats and/or
  iii) quaternary imidazolines of formula (Tkat2)

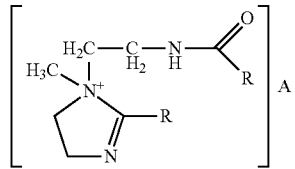

in which the radicals R independently of one another each represent a saturated or unsaturated, linear or branched hydrocarbon radical having a chain length of 8 to 30 carbon atoms and A represents a physiologically acceptable anion, and/or
  iv) amines and/or cationized amines and/or
  v) poly(methacryloyloxyethyltrimethylammonium) compounds and/or
  vi) quaternized cellulose derivatives, in particular Polyquaternium-10, Polyquaternium-24, Polyquaternium-27, Polyquaternium-67, Polyquaternium-72, and/or
  vii) cationic alkyl polyglycosides and/or
  viii) cationized honey and/or
  ix) cationic guar derivatives and/or
  x) polymeric dimethyldiallylammonium salts and copolymers thereof with esters and amides of acrylic acid and methacrylic acid, in particular Polyquaternium-7, and/or
  xi) copolymers of vinylpyrrolidone with quaternized derivatives of dialkylaminoalkyl acrylate and methacrylate, in particular Polyquaternium-11, and/or
  xii) vinylpyrrolidone-vinylimidazolium methochloride copolymers, in particular Polyquaternium-16, and/or
  xiii) quaternized polyvinyl alcohol and/or
  xiv) Polyquaternium-74,
  xv) cationic alkyl oligoglucosides and/or
  xvi) Polyquaternium-71
and mixtures thereof.

Esterquats according to the formula (Tkat1-2) are the first group of quaternary ammonium compounds.

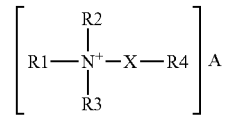 (Tkat1-2)

In this formula, the radicals R1, R2 and R3 are each independent of one another and may be identical or different. The radicals R1, R2 and R3 denote:
  a branched or unbranched alkyl radical having 1 to 4 carbon atoms, which may include at least one hydroxyl group, or
  a saturated or unsaturated, branched or unbranched or a cyclic saturated or unsaturated alkyl radical having 6 to 30 carbon atoms, which may include at least one hydroxyl group, or
  an aryl or alkaryl radical, for example phenyl or benzyl, the radical (—X—R4), with the proviso that at most 2 of the radicals R1, R2 or R3 may represent this radical:
  The radical (—X—R4) is present at least 1 to 3 times.
  Herein, X represents:
1) —(CH2)n-, where n=1 to 20, preferably n=1 to 10 and particularly preferably n=1 to 5, or
2) —(CH2-CHR5-O)n-, where n=1 to 200, preferably 1 to 100, particularly preferably 1 to 50 and particularly preferably 1 to 20 with R5 denoting hydrogen, methyl or ethyl,
3) a hydroxyalkyl group having one to four carbon atoms, which may be branched or unbranched, and which includes at least one and at most 3 hydroxyl groups. Examples of —X— are: —CHOH, —CHCH$_2$OH, —CH$_2$CHOH, —COHCHOH, —CHOHCOH, —CHCHOHCH$_3$, —CH$_2$COHCH$_3$, —CH$_2$CHOHCH$_2$—, —C(CH$_2$OH)$_2$, —CH$_2$CHOHCH$_2$OH, —CH$_2$CH$_2$CHOH, —CH$_2$COHCH$_3$ and hydroxybutyl radicals, wherein the bonding of —X— to R4 stems from the free valency of the carbon atom in question
and R4 represents:
1) R6-O—CO—, in which R6 is a saturated or unsaturated, branched or unbranched or a cyclic saturated or unsaturated alkyl radical having 6 to 30 carbon atoms, which may include at least one hydroxyl group, and which may optionally also be oxethylated with 1 to 100 ethylene oxide units and/or 1 to 100 propylene oxide units, or
2) R7-CO—, in which R7 is a saturated or unsaturated, branched or unbranched or a cyclic saturated or unsaturated alkyl radical having 6 to 30 carbon atoms, which may include at least one hydroxyl group, and which may optionally also be oxethylated with 1 to 100 ethylene oxide units and/or 1 to 100 propylene oxide units,
and A represents a physiologically acceptable organic or inorganic anion and is defined at this point as representative of all the structures described below. The anion of all the described cationic compounds is selected from the halide ions, fluoride, chloride, bromide, iodide, sulfates of general formula RSO$_3^-$, in which R has the meaning of saturated or unsaturated alkyl radicals having 1 to 4 carbon atoms, or anionic radicals of organic acids such as maleate, fumarate, oxalate, tartrate, citrate, lactate or acetate.

Such products are sold for example under the brand names Rewoquat®, Stepantex®, Dehyquart®, Armocare® and Akypoquat®. The products Armocare® VGH-70, Dehyquart® F-75, Dehyquart® C-4046, Dehyquart® L80, Dehyquart® F-30, Dehyquart® AU-35, Rewoquat® WE18, Rewoquat® WE38 DPG, Stepantex® VS 90 and Akypoquat® 131 are examples of these esterquats.

Other compounds of formula (Tkat1-2) which are particularly preferred according to the invention fall under the formula (Tkat1-2.1), cationic betaine esters.

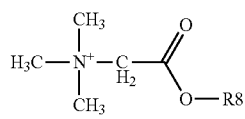
(Tkat1-2.1)

R8 corresponds in its meaning to R7.

Particular preference is given to the esterquats bearing the trade names Armocare® VGH-70, as well as Dehyquart® F-75, Dehyquart® L80, Stepantex® VS 90 and Akypoquat® 131.

Quaternary imidazoline compounds are a further group. The formula (Tkat2) shown below illustrates the structure of these compounds.

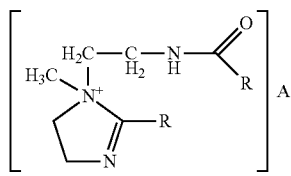
(Tkat2)

The radicals R independently of one another each represent a saturated or unsaturated, linear or branched hydrocarbon radical having a chain length of 8 to 30 carbon atoms. The preferred compounds of formula (Tkat2) include the same hydrocarbon radical for each instance of R. The chain length of the radicals R is preferably 12 to 21 carbon atoms. A represents an anion as described above. Particular examples according to the invention are available for example under the INCII names Quaternium-27, Quaternium-72, Quaternium-83 and Quaternium-91. Quaternium-91 is most preferred according to the invention.

Cationic surfactants of formula (Tkat1-1) are the third group of preferred quaternary ammonium compounds.

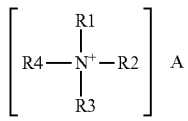
(Tkat1)

In the formula (Tkat1), R1, R2, R3 and R4 independently of one another each represent hydrogen, a methyl group, a phenyl group, a benzyl group, a saturated, branched or unbranched alkyl radical having a chain length of 8 to 30 carbon atoms, which may optionally be substituted with one or more hydroxyl groups. A represents a physiologically acceptable anion, for example halides such as chloride or bromide as well as methosulfates.

Examples of compounds of formula (Tkat1) are lauryl trimethyl ammonium chloride, cetyl trimethyl ammonium chloride, cetyl trimethyl ammonium bromide, cetyl trimethyl ammonium methosulfate, dicetyl dimethyl ammonium chloride, tricetyl methyl ammonium chloride, stearyl trimethyl ammonium chloride, distearyl dimethyl ammonium chloride, lauryl dimethyl benzyl ammonium chloride, behenyl trimethyl ammonium chloride, behenyl trimethyl ammonium bromide, behenyl trimethyl ammonium methosulfate. Particular preference is given to compounds having at least one cetyl or behenyl radical in the molecule. Cetyl trimethyl ammonium and behenyl trimethyl ammonium salts are extremely preferred, cetyl trimethyl ammonium chloride and behenyl trimethyl ammonium chloride being the most preferred of all.

Extremely preferred methods are characterized in that the styling agents include 0.15 to 5 wt. %, preferably 0.11 to 2.5 wt. %, more preferably 0.12 to 2 wt. %, even more preferably 0.13 to 1 wt. % and in particular 0.15 to 0.75 wt. % alkyl trimethyl ammonium chloride(s), in particular cetyl trimethyl ammonium chloride.

The last group of quaternary ammonium compounds are amines and/or cationized amines, in particular amidoamines and/or cationized amidoamines. In one particularly preferred embodiment of the invention, the styling agents used in the method according to the invention include, in addition to at least one other of the quaternary ammonium compounds, at least one amine and/or cationized amine, in particular one amidoamine and/or one cationized amidoamine, having the following structural formulae:

$$R1-NH-(CH_2)_n-N^+R^2R^3R^4A$$ (Tkat3)

in which R1 is an acyl or alkyl radical having 6 to 30 C atoms, which may be branched or unbranched, saturated or unsaturated, and wherein the acyl radical and/or the alkyl radical may include at least one OH group, and R2, R3 and R4 independently of one another are each
1) hydrogen or
2) an alkyl radical having 1 to 4 C atoms, which may be identical or different, saturated or unsaturated, and
3) a branched or unbranched hydroxyalkyl group having one to 4 carbon atoms with at least one and at most three hydroxyl groups, for example —CH$_2$OH, —CH$_2$CH$_2$OH, —CHOHCHOH, —CH$_2$CHOHCH$_3$, —CH(CH$_2$OH)$_2$, —COH(CH$_2$OH)$_2$, —CH$_2$CHOHCH$_2$OH, —CH$_2$CH$_2$CH$_2$OH and hydroxybutyl radicals, and A is an anion as described above and
n is a whole number between 1 and 10.

Preference is given to a composition in which the amine and/or the quaternized amine according to the general formula (Tkat3) is an amidoamine and/or a quaternized amidoamine, in which R1 denotes a branched or unbranched, saturated or unsaturated acyl radical having 6 to 30 C atoms, which may include at least one OH group. Preference is given here to a fatty acid radical from oils and waxes, in particular from natural oils and waxes. As examples, mention may be made of lanolin, beeswax or candelilla wax.

Preference is also given to those amidoamines and/or quaternized amidoamines in which R2, R3 and/or R4 in the formula (Tkat3) denote a radical according to the general formula CH$_2$CH$_2$OR$_5$, in which R5 can have the meaning of alkyl radicals having 1 to 4 carbon atoms, hydroxyethyl or hydrogen. The preferred value of n in the general formula (Tkat8) is a whole number between 2 and 5.

The alkylamidoamines may be present both as such and may be converted by protonation in suitably acidic solution into a quaternary compound in the composition. The cationic alkylamidoamines are preferred according to the invention.

Examples of such commercial products according to the invention are Witcamine® 100, Incromine® BB, Mackine® 401 and other Mackine® types, Adogen® S18V and, as permanently cationic aminoamines: Rewoquat® RTM 50, Empigen® CSC, Swanol® Lanoquat DES-50, Rewoquat® UTM 50, Schercoquat® BAS, Lexquat® AMG-BEO or Incroquat® Behenyl HE.

All of the abovementioned quaternary ammonium compounds are cationic surfactants and may be used individually or in any combination with one another, these being included in amounts of 0.01 to 10 wt. %, preferably amounts of 0.01 to 7.5 wt. % and very particularly preferably amounts of 0.1 to 5.0 wt. %. The best results are obtained with amounts of 0.1 to 3.0 wt. %, in each case based on the total composition of the respective styling agent used in the method according to the invention. These amounts are also not undershot or exceeded if mixtures of the cationic surfactants are used.

A further preferred group of ingredients of the styling agents used in the method according to the invention are vitamins, provitamins or vitamin precursors.

Particular preference is given to vitamins, provitamins and vitamin precursors which are assigned to the groups A, B, C, E, F and H.

The group of substances designated as vitamin A includes retinol (vitamin $A_1$) and also 3,4-didehydroretinol (vitamin $A_2$). β-Carotene is the provitamin of retinol. As vitamin A components, mention may be made according to the invention of, for example, vitamin A acid and esters thereof, vitamin A aldehyde and vitamin A alcohol and esters thereof such as the palmitate and acetate. The agents according to the invention include the vitamin A components preferably in amounts of 0.05-1 wt. %, based on the total preparation.

The vitamin B group or the vitamin B complex includes inter alia:
vitamin $B_1$ (thiamine)
vitamin $B_2$ (riboflavin)
vitamin $B_3$. The compounds nicotinic acid and nicotinamide (niacinamide) are often included under this designation. Nicotinamide is preferred according to the invention and is included in the agents used according to the invention preferably in amounts of 0.05 to 1 wt. %, based on the total agent.
vitamin $B_5$ (pantothenic acid, panthenol and pantolactone). In the context of this group, use is preferably made of panthenol and/or pantolactone. Derivatives of panthenol which can be used according to the invention are in particular the esters and ethers of panthenol as well as cationically derivatized panthenols. Individual representatives are, for example, panthenol triacetate, panthenol monoethyl ether and the monoacetate thereof, as well as cationic panthenol derivatives. Pantothenic acid will be used in the present invention preferably as a derivative in the form of the more stable calcium salts and sodium salts (Ca pantothenate, Na pantothenate).
vitamin $B_6$ (pyridoxine as well as pyridoxamine and pyridoxal).

The aforementioned compounds of the vitamin B type, in particular vitamin $B_3$, $B_5$ and $B_6$, are included in the agents according to the invention preferably in amounts of 0.05-10 wt. %, based on the total agent. Amounts of 0.1-5 wt. % are particularly preferred.

Vitamin C (ascorbic acid). Vitamin C will be used in the styling agents used in the method according to the invention preferably in amounts of 0.1 to 3 wt. %, based on the total agent. Use in the form of the palmitate ester, the glucosides or phosphates may be preferred. Use in combination with tocopherols may likewise be preferred.

Vitamin E (tocopherols, in particular α-tocopherol). Tocopherol and the derivatives thereof, including in particular the esters such as the acetate, the nicotinate, the phosphate and the succinate, are included in the styling agents used in the method according to the invention preferably in amounts of 0.05-1 wt. %, based on the total agent.

Vitamin F. The term "vitamin F" is usually understood to mean essential fatty acids, in particular linoleic acid, linolenic acid and arachidonic acid.

Vitamin H. The compound (3aS,4S,6aR)-2-oxohexahydrothienol[3,4-d]imidazole-4-valeric acid is designated as vitamin H, for which the trivial name biotin has become accepted. Biotin is included in the agents according to the invention preferably in amounts of 0.0001 to 1.0 wt. %, in particular in amounts of 0.001 to 0.01 wt. %.

The compositions according to the invention preferably include vitamins, provitamins and vitamin precursors from the groups A, B, E and H. Panthenol, pantolactone, pyridoxine and derivatives thereof as well as nicotinamide and biotin are particular preferred.

One particularly preferred group of ingredients in the styling agents used in the method according to the invention are the following betaines: carnitine, carnitine tartrate, carnitine magnesium citrate, acetyl carnitine, betalain, 1,1-dimethylproline, choline, choline chloride, choline bitartrate, choline dihydrogen citrate and the compound N,N,N-trimethylglycine cited in the literature as a betaine.

Carnitine, histidine, choline and betaine are used with preference. In one particularly preferred embodiment of the invention, L-carnitine tartrate is used as an active ingredient.

In a further embodiment which is preferred according to the invention, the styling agents used in the method according to the invention include bioquinones. In the styling agents used in the method according to the invention, suitable bioquinones are to be understood to mean one or more ubiquinones and/or plastoquinones. The ubiquinones which are preferred according to the invention have the following formula:

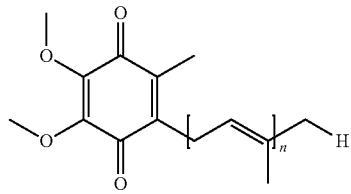

where n=6, 7, 8, 9 or 10.

The coenzyme Q-10 is most preferred here.

Preferred styling agents used in the method according to the invention include purine and/or purine derivatives in relatively narrow quantitative ranges. Here, styling agents used in the method according to the invention are preferably characterized in that they contain, based on their weight, 0.001 to 2.5 wt. %, preferably 0.0025 to 1 wt. %, particularly preferably 0.005 to 0.5 wt. % and in particular 0.01 to 0.1 wt. % purine(s) and/or purine derivative(s). Cosmetic agents which are preferred according to the invention are characterized in that they include purine, adenine, guanine, uric acid, hypoxanthine, 6-purinethiol, 6-thioguanine, xanthine, caffeine, theobromine or theophylline. In cosmetic preparations for the hair, caffeine is most preferred.

In another preferred embodiment of the present invention, the styling agent used in the method according to the invention includes ectoine ((S)-2-methyl-1,4,5,6-tetrahydro-4-pyrimidinecarboxylic acid).

Particularly preferred according to the invention are agents which contain, based on their weight, 0.00001 to 10.0 wt. %, preferably 0.0001 to 5.0 wt. % and in particular 0.001 to 3 wt. % of the active ingredients from the group formed of carnitine, coenzyme Q-10, ectoine, a vitamin of the B series, a purine and derivatives thereof or physiologically acceptable salts.

One care additive which is very particularly preferred in the styling agents used in the method according to the invention is taurine. Taurine is understood to mean exclusively 2-aminoethanesulfonic acid, and a derivative is understood to mean the explicitly mentioned derivatives of taurine. The derivatives of taurine will be understood to mean N-monomethyl taurine, N,N-dimethyl taurine, taurine lysylate, taurine tartrate, taurine ornithate, lysyl taurine and ornithyl taurine.

Particular preference is given to styling agents used in the method according to the invention which contain, based on their weight, 0.0001 to 10.0 wt. %, preferably 0.0005 to 5.0 wt. %, particularly preferably 0.001 to 2.0 wt. % and in particular 0.001 to 1.0 wt. % of taurine and/or a derivative of taurine.

By using plant extracts as care substances, the styling agents used in the method according to the invention can be formulated in a way that is in particular harmony with nature and is nevertheless very effective in terms of their care performance. It may optionally even be possible to omit the preservatives which are otherwise customary. According to the invention, particular preference is given to the extracts of green tea, oak bark, stinging nettle, witch hazel, hops, henna, chamomile, burdock root, horsetail, hawthorn, lime blossom, almonds, aloe vera, spruce needles, horse chestnut, sandalwood, juniper, coconut, mango, apricot, lime, wheat, kiwi, melon, orange, grapefruit, sage, rosemary, birch, mallow, valerian, cuckoo flower, wild thyme, yarrow, thyme, lemon balm, restharrow, coltsfoot, marshmallow, meristem, *ginseng*, coffee, cocoa, moringa, ginger root and Ayurvedic plant extracts such as, for example, *Aegle Marmelos* (Bilwa), *Cyperus Rotundus* (Nagar Motha), *Emblica Officinalis* (Amalki), *Morida Citrifolia* (Ashyuka), *Tinospora Cordifolia* (Guduchi), *Santalum album* (Chandana), *Crocus Sativus* (Kumkuma), *Cinnamonum Zeylanicum* and *Nelumbo Nucifera* (Kamala), sweet grasses such as wheat, barley, rye, oats, spelt, maize, the various types of millet (sorghum, crabgrass, foxtail millet as examples), sugar cane, ryegrass, meadow foxtail, oat grass, bentgrass, meadow fescue, moor grass, bamboo, cotton grass, fountain grasses, Andropogonodeae (*Imperata Cylindrica* also called cogon grass), buffalo grass, cord grass, Bermuda grasses, love grass, Cymbopogon (lemongrass), Oryzeae (rice), Zizania (wild rice), marram grass, blue oat grass, creeping soft grass, quaking grasses, meadow grasses, couch grasses and *Echinacea*, in particular *Echinacea purpurea* (L.) Moench, all types of wine as well as pericarp of *Litchie chinensis*.

The plant extracts can be used according to the invention both in pure form and in diluted form. If they are used in diluted form, they usually include approximately 2-80 wt. % active substance and the solvent is the extraction agent or mixture of extraction agents used for their extraction.

It has been found that certain proteolipids further enhance the effect of the method according to the invention. As a further ingredient, the styling agents used in the method according to the invention may include at least one proteolipid of formula (P-I)

R'—X—R" (P-I), in which
R' represents a straight-chain or branched, saturated or unsaturated hydrocarbon radical having 11 to 24 carbon atoms, R" denotes a protein, a peptide or a protein hydrolysate,
X represents —C(O)O— or —N$^+$(R$^{III}$$_2$)R$^{IV}$— or —N(R$^{III}$)R$^{IV}$— or —C(O)—N(R$^V$)R$^{VI}$—,
R$^{III}$ denotes —(CH$_2$)$_x$—CH$_3$ where x=0-22 and
R$^{IV}$ denotes —CH$_2$—CH(OH)—CH$_2$— or —(CH$_2$)$_x$— where x=0-22;
R$^V$ and R$^V$ independently of one another represent —H or —(CH$_2$)$_x$—CH$_3$ where x=0-22;
with the proviso that R" represents keratin or a keratin hydrolysate when X represents —C(O)O—.

The proteolipids are preferably used within certain amounts in the styling agents used in the method according to the invention. Preferred styling agents used in the method according to the invention contain, based on their weight, 0.01 to 10 wt. %, preferably 0.02 to 5 wt. %, particularly preferably 0.05 to 2.5 wt. %, more preferably 0.1 to 1 wt. % and in particular 0.15 to 0.5 wt. % proteolipid(s).

The radical R" in formula (P-I) represents a peptide or a protein or a protein hydrolysate. If X=—C(O)O—, R" is selected from the group consisting of keratin or keratin hydrolysate.

Preferred radicals R" are oligopeptides which have at least one amino acid sequence Glu-Glu-Glu

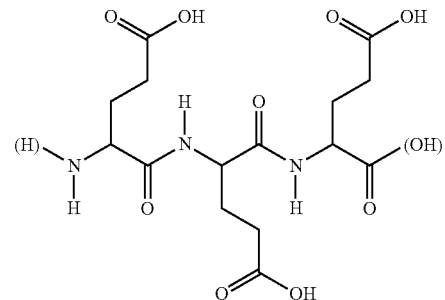

wherein the amino group may be in free or protonated form and the carboxyl groups may be in free or deprotonated form.

In this as in all the formulae below, the bracketed hydrogen atom of the amino group and the bracketed hydroxyl group of the acid function mean that the groups in question may be present as such (this then making it an oligopeptide having the relevant number of amino acids as shown (3 in the above formula), or else that the amino acid sequence exists in an oligopeptide which comprises further amino acids—depending on where the further amino acid(s) is/are bonded, the bracketed constituents of the above formula are replaced by the further amino acid residue(s).

In the context of the present invention, oligopeptides are condensation products of amino acids which are linked by peptide bonds in the manner of an acid amide and which comprise at least 3 and at most 25 amino acids.

In preferred styling agents of the embodiment described above which are used in the method according to the invention, the oligopeptide (=the radical R") comprises 5 to 15 amino acids, preferably 6 to 13 amino acids, particularly preferably 7 to 12 amino acids and in particular 8, 9 or 10 amino acids.

Depending on whether further amino acids are bound to the sequence Glu-Glu-Glu, and depending on the type of these amino acids and also depending on the choice of radicals R' and optionally R$^{III}$ and R$^{IV}$, the molecular weight of the proteolipid included in the agents according to the invention may vary. Preferred styling agents used in the method according to the invention are characterized in that the proteolipid has a molecular weight of 1000 to 30,000 Da, preferably 1250 to 25,000 Da, particularly preferably 1500 to 20,000 Da and in particular 2000 to 15,000 Da.

As the radical R", use is preferably made of oligopeptides which do not consist solely of the three glutamic acids but rather have further amino acids bound to this sequence. These further amino acids are preferably selected from certain amino acids, while certain other representatives are less preferred according to the invention.

For instance, it is preferred if the radical R" of the proteolipids used in the styling agents used in the method according to the invention includes no methionine. It is further preferred if the radical R" of the proteolipids used in the agents according to the invention includes no cysteine and/or cystine.

It is further preferred if the radical R" of the proteolipids used in the styling agents used in the method according to the invention includes no aspartic acid and/or asparagine. It is further preferred if the radical R" of the proteolipids used in the agents according to the invention includes no serine and/or threonine.

In contrast, it is preferred if the radical R" of the proteolipids used in the styling agents used in the method according to the invention includes tyrosine. It is further preferred if the radical R" of the proteolipids used in the agents according to the invention includes leucine. It is further preferred if the radical R" of the proteolipids used in the agents according to the invention includes isoleucine. It is further preferred if the radical R" of the proteolipids used in the styling agents used in the method according to the invention includes arginine. It is further preferred if the radical R" of the proteolipids used in the styling agents used in the method according to the invention includes valine.

Oligopeptides which are particularly preferred as the radical R", and amino acid sequences included in the preferred oligopeptides, will be described below:

One particularly preferred oligopeptide additionally includes tyrosine, which is preferably bound via its acid function to the Glu-Glu-Glu sequence. Preferred styling agents used in the method according to the invention are therefore characterized in that the oligopeptide included as the radical R" in the proteolipids of formula (I) has at least one amino acid sequence Tyr-Glu-Glu-Glu

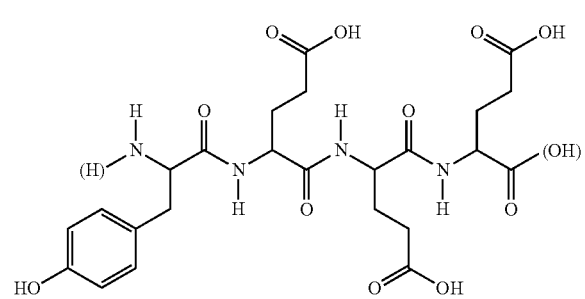

wherein the amino group may be in free or protonated form and the carboxyl groups may be in free or deprotonated form.

A further particularly preferred oligopeptide additionally includes isoleucine, which is preferably bound via its amino function to the Glu-Glu-Glu sequence. Preferred styling agents used in the method according to the invention are therefore characterized in that the oligopeptide included as the radical R" in the proteolipids of formula (I) has at least one amino acid sequence Glu-Glu-Glu-Ile

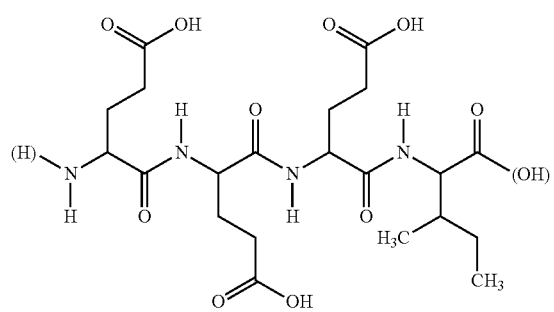

wherein the amino group may be in free or protonated form and the carboxyl groups may be in free or deprotonated form.

Oligopeptides which include both of the aforementioned amino acids (tyrosine and isoleucine) are preferred according to the invention. Preference is given to styling agents used in the method according to the invention in which the oligopeptide included as the radical R" in the proteolipids of formula (I) has at least one amino acid sequence Tyr-Glu-Glu-Glu-Ile

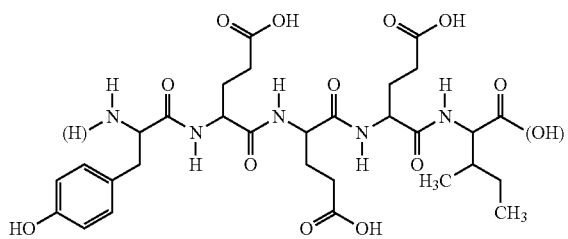

wherein the amino group may be in free or protonated form and the carboxyl groups may be in free or deprotonated form.

More preferred oligopeptides additionally include arginine, which is preferably bound to isoleucine. Preferred styling agents used in the method according to the invention are therefore characterized in that the oligopeptide included as the radical R" in the proteolipids of formula (I) has at least one amino acid sequence Tyr-Glu-Glu-Glu-Ile-Arg

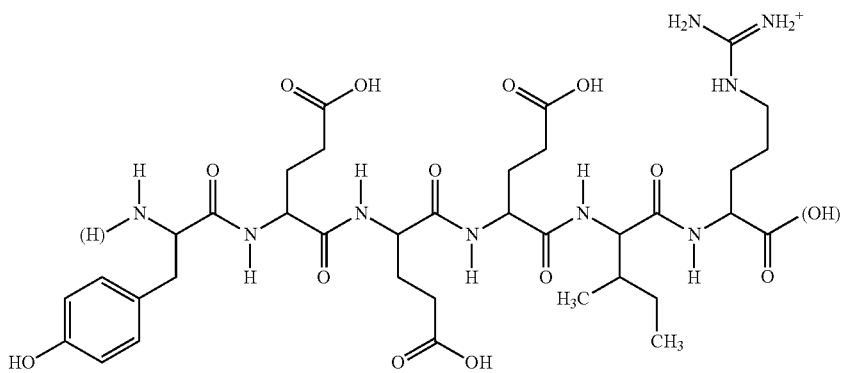

wherein the amino groups may be in free or protonated form and the carboxyl groups may be in free or deprotonated form.

Yet more preferred oligopeptides additionally include valine, which is preferably bound to the arginine. Preferred styling agents used in the method according to the invention are therefore characterized in that the oligopeptide included as the radical R" in the proteolipids of formula (I) has at least one amino acid sequence Tyr-Glu-Glu-Glu-Ile-Arg-Val

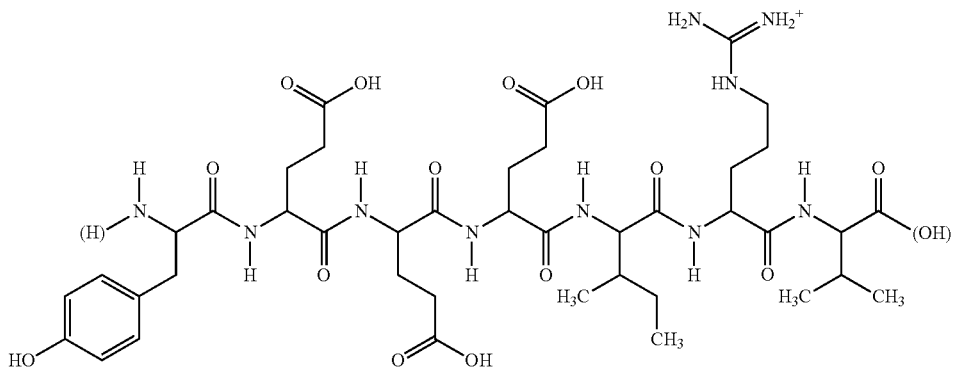

wherein the amino groups may be in free or protonated form and the carboxyl groups may be in free or deprotonated form.

Yet more preferred oligopeptides additionally include leucine, which is preferably bound to valine. Preferred styling agents used in the method according to the invention are therefore characterized in that the oligopeptide included as the radical R" in the proteolipids of formula (I) has at least one amino acid sequence Tyr-Glu-Glu-Glu-Ile-Arg-Val-Leu

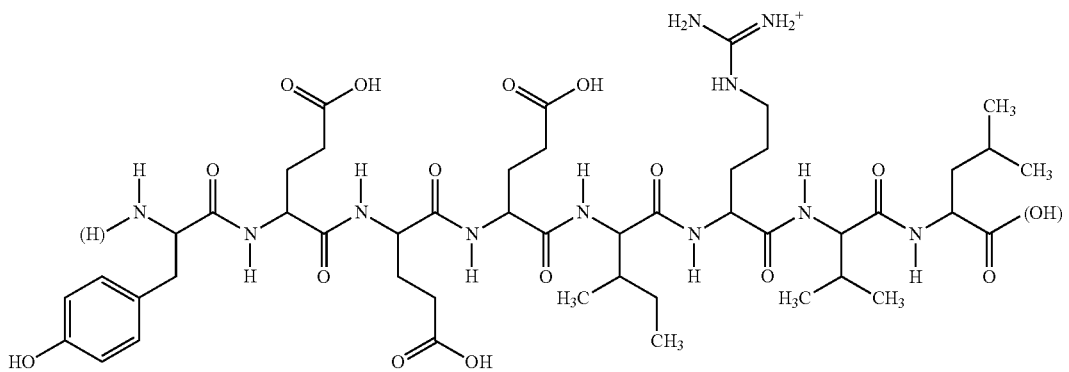

wherein the amino groups may be in free or protonated form and the carboxyl groups may be in free or deprotonated form.

Particularly preferred oligopeptides additionally include leucine, which is preferably bound to the tyrosine. Preferred styling agents used in the method according to the invention are therefore characterized in that the oligopeptide included as the radical R" in the proteolipids of formula (I) has at least one amino acid sequence Leu-Tyr-Glu-Glu-Glu-Ile-Arg-Val-Leu

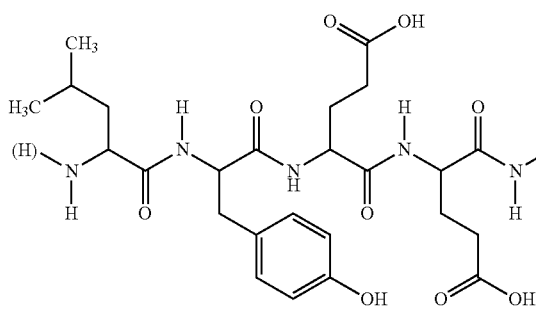

wherein the amino groups may be in free or protonated form and the carboxyl groups may be in free or deprotonated form.

To sum up, particular preference is given to styling agents used in the method according to the invention which include at least one proteolipid of formula (I) in which R" has at least one amino acid sequence Leu-Tyr-Glu-Glu-Glu-Ile-Arg-Val-Leu

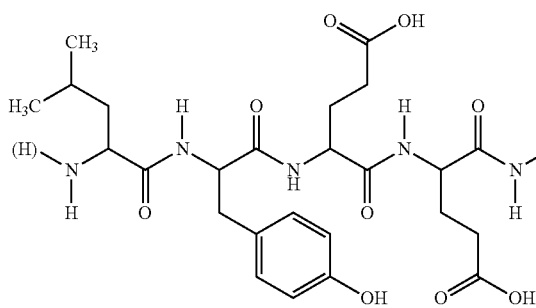

wherein the amino groups may be in free or protonated form and the carboxyl groups may be in free or deprotonated form.

As already mentioned, R" is selected from the group consisting of keratin or keratin hydrolysate when X=—C(O)O—.

In all other cases, the radical R" in formula (P-I) may represent a peptide or a protein or a protein hydrolysate, preference being given to protein hydrolysates. Protein hydrolysates are product mixtures which are obtained by acid-catalyzed, base-catalyzed or enzyme-catalyzed reduction of proteins. Protein hydrolysates of both plant and animal origin may be used according to the invention.

Animal protein hydrolysates are for example hydrolysates of elastin, collagen, keratin, silk and milk protein, which may also be present in the form of salts. Such products are sold for example under the brand names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

According to the invention, preference is given to the use of protein hydrolysates of plant origin, for example soy, almond, rice, pea, potato and wheat protein hydrolysates.

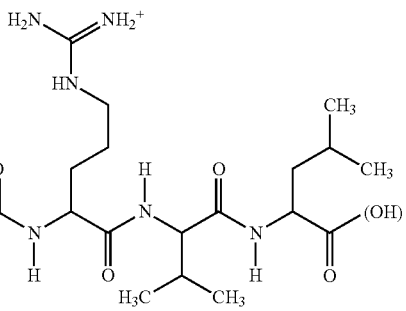

Such products are available for example under the brand names Gluadin® (Cognis), DiaMin® (Diamalt), Lexein® (Inolex) and Crotein® (Croda).

Preferably, the radical R" will be selected from keratin or keratin hydrolysates regardless of the choice of X in formula (P-I). Preferred cosmetic agents according to the invention

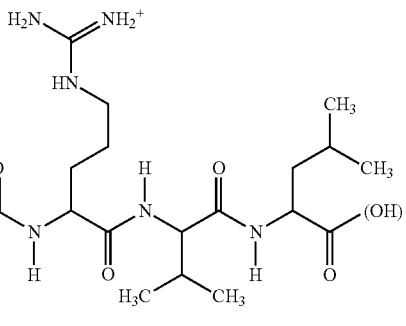

are characterized in that they include at least one proteolipid of formula (P-I) in which R" represents keratin or a keratin hydrolysate.

Particular preference is given to styling agents used in the method according to the invention which include at least one proteolipid of formula (P-I) in which $R^{III}$ denotes —$CH_3$ and $R^{IV}$ represents —$(CH_2)_x$— where x=0, 1, 2, 3, 4, 5, 6, 7, 8.

Furthermore, particularly preferred styling agents used in the method according to the invention are characterized in that they include at least one proteolipid of formula (I) in which X represents —$N^+(CH_3)_2$—$CH_2$—CH(OH)—$CH_2$— and R' represents —$(CH_2)_{17}$—$CH_3$.

More preferred styling agents used in the method according to the invention are characterized in that they include at least one proteolipid of formula (P-l) in which X represents —C(O)—O— and R' represents —(CH$_2$)$_{17}$—CH$_3$.

It has proven to be advantageous to use protein hydrolysates in addition to the proteolipids. Said protein hydrolysates enhance the effect of the proteolipids and are for their part enhanced in their effects. The protein hydrolysates have been described in detail above as the radical R". To sum up, preference is given to styling agents used in the method according to the invention which additionally contain, based on their weight, 0.01 to 10 wt. %, preferably 0.05 to 7 wt. %, particularly preferably 0.1 to 5 wt. %, more preferably 0.25 to 2.5 wt. % and in particular 0.5 to 2.0 wt. % protein hydrolysate(s), preferably keratin hydrolysate(s).

In step (ii) of the method according to the invention, the fibers are not rinsed, that is to say the styling agent remains on the fibers during the styling. The fibers may be styled in the wet state, but it is also possible to dry the fibers after the styling agent has been applied and before the styling operation.

Preferred methods according to the invention are characterized in that the fibers are dried in step (ii).

The drying may take place by rubbing with a towel or preferably by applying hot air, in particular by blow-drying.

After the treatment with the styling agent, the fibers are deformed {step (iii) of the method according to the invention}. The deformation in step (iii) may be heat-assisted, for example by means of heated curlers or, with particular preference, by using straightening irons.

Methods according to the invention in which the fibers in step (iii) are subjected to a heat treatment at a temperature of 50° C. to 350° C. (preferably 80° C. to 280° C., particularly preferably 100° C. to 250° C., more preferably 140° C. to 220° C.) are preferred according to the invention.

A further subject matter of the present invention is the use of carbocisteine and/or salts thereof for protecting keratin fibers, in particular human hair, during styling methods.

A further subject matter of the present invention is the use of carbocisteine and/or salts thereof for preventing electrostatic charging and hydrophilization of keratin fibers, in particular human hair, during styling methods.

For preferred embodiments of the uses according to the invention, what has been stated above in relation to the methods according to the invention applies mutatis mutandis.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for styling keratin fibers, in which
   (i) applying a styling agent comprising carbocisteine or a salt thereof to the keratin fibers and left thereon for a leave-in time,
   (ii) the fibers, after the leave-in time,
      are not rinsed,
      are optionally dried,
   (iii) the fibers are mechanically deformed from exposure to heat
   wherein the styling agent comprises, based on its total weight, 30 to 95 wt % water;
   and based on its total weight, 0.15 to 7.5 wt % quaternary ammonium compound(s) selected from the group
      i) tetraalkylammonium halides;
      ii) esterquats;
      iii) quaternary imidazolines of formula (Tkat2)

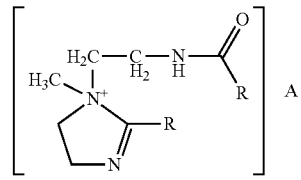

in which the radicals R independently of one another each represent a saturated or unsaturated, linear or branched hydrocarbon radical having a chain length of 8 to 30 carbon atoms and A represents a physiologically acceptable anion;
      iv) amines;
      v) poly(methacryloyloxyethyltrimethylammonium) compounds
      vi) quaternized cellulose derivatives,
      vii) cationic alkyl polyglycosides;
      viii) cationized honey;
      ix) cationic guar derivatives;
      x) polymeric dimethyldiallylammonium salts and copolymers thereof with esters and amides of acrylic acid and methacrylic acid;
      xi) copolymers of vinylpyrrolidone with quaternized derivatives of dialkylaminoalkyl acrylate and methacrylate;
      xii) vinylpyrrolidone-vinylimidazolium methochloride copolymers;
      xiii) quaternized polyvinyl alcohol;
      xiv) Polyquaternium-74;
      xv) cationic alkyl oligoglucosides;
      xvi) Polyquaternium-71;
   and mixtures thereof.

2. The method according to claim 1, wherein the styling agent comprises, based on its total weight, 0.01 to 10 wt % carbocisteine.

3. The method according to claim 1, wherein the styling agent comprises, based on its total weight, 0.1 to 7.5 wt %, carbocisteine.

4. The method according to claim 1, wherein the styling agent comprises, based on its total weight, 0.25 to 5 wt %, carbocisteine.

5. The method according to claim 1, wherein the styling agent comprises, based on its total weight, 0.5 to 2.5 wt % carbocisteine.

6. The method according to claim 1, wherein the styling agent comprises, based on its total weight, 0.55 to 2 wt % carbocisteine.

7. The method according to claim 1, wherein the styling agent comprises, based on its total weight 40 to 92.5 wt % water.

8. The method according to claim 1, wherein the styling agent comprises, based on its total weight 50 to 90 wt % water.

9. The method according to claim 1, wherein the styling agent comprises, based on its total weight, 0.15 to 5 wt %, quaternary ammonium compound(s) selected from the group
i) tetraalkylammonium halides;
ii) esterquats;
iii) quaternary imidazolines of formula (Tkat2)

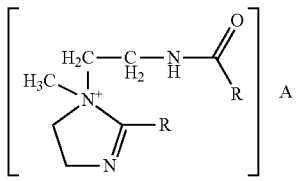

in which the radicals R independently of one another each represent a saturated or unsaturated, linear or branched hydrocarbon radical having a chain length of 8 to 30 carbon atoms and A represents a physiologically acceptable anion;
iv) amines
v) poly(methacryloyloxyethyltrimethylammonium) compounds
vi) quaternized cellulose derivatives,
vii) cationic alkyl polyglycosides;
viii) cationized honey;
ix) cationic guar derivatives;
x) polymeric dimethyldiallylammonium salts and copolymers thereof with esters and amides of acrylic acid and methacrylic acid;
xi) copolymers of vinylpyrrolidone with quaternized derivatives of dialkylaminoalkyl acrylate and methacrylate;
xii) vinylpyrrolidone-vinylimidazolium methochloride copolymers;
xiii) quaternized polyvinyl alcohol;
xiv) Polyquaternium-74;
xv) cationic alkyl oligoglucosides;
xvi) Polyquaternium-71;
and mixtures thereof.

10. The method according to claim 1, wherein the styling agent comprises, based on its total weight, 0.25 to 3 wt % quaternary ammonium compound(s) selected from the group
i) tetraalkylammonium halides;
ii) esterquats;
iii) quaternary imidazolines of formula (Tkat2)

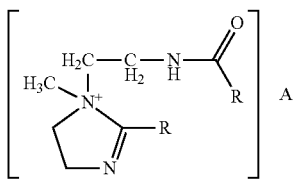

in which the radicals R independently of one another each represent a saturated or unsaturated, linear or branched hydrocarbon radical having a chain length of 8 to 30 carbon atoms and A represents a physiologically acceptable anion;
iv) amines;
v) poly(methacryloyloxyethyltrimethylammonium) compounds
vi) quaternized cellulose derivatives
vii) cationic alkyl polyglycosides;
viii) cationized honey;
ix) cationic guar derivatives;
x) polymeric dimethyldiallylammonium salts and copolymers thereof with esters and amides of acrylic acid and methacrylic acid;
xi) copolymers of vinylpyrrolidone with quaternized derivatives of dialkylaminoalkyl acrylate and methacrylate;
xii) vinylpyrrolidone-vinylimidazolium methochloride copolymers;
xiii) quaternized polyvinyl alcohol;
xiv) Polyquaternium-74;
xv) cationic alkyl oligoglucosides;
xvi) Polyquaternium-71;
and mixtures thereof.

11. The method according to claim 1, wherein the styling agent comprises, based on its total weight, 0.3 to 1 wt % quaternary ammonium compound(s) selected from the group
i) tetraalkylammonium halides;
ii) esterquats;
iii) quaternary imidazolines of formula (Tkat2)

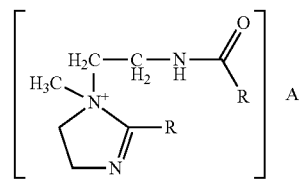

in which the radicals R independently of one another each represent a saturated or unsaturated, linear or branched hydrocarbon radical having a chain length of 8 to 30 carbon atoms and A represents a physiologically acceptable anion;
iv) amines;
v) poly(methacryloyloxyethyltrimethylammonium) compounds
vi) quaternized cellulose derivatives
vii) cationic alkyl polyglycosides;
viii) cationized honey;
ix) cationic guar derivatives;
x) polymeric dimethyldiallylammonium salts and copolymers thereof with esters and amides of acrylic acid and methacrylic acid;
xi) copolymers of vinylpyrrolidone with quaternized derivatives of dialkylaminoalkyl acrylate and methacrylate;
xii) vinylpyrrolidone-vinylimidazolium methochloride copolymers;
xiii) quaternized polyvinyl alcohol;
xiv) Polyquaternium-74;
xv) cationic alkyl oligoglucosides;
xvi) Polyquaternium-71;
and mixtures thereof.

12. The method according to claim 1, wherein the fibers are dried in step (ii).

13. The method according to claim 1, wherein the fibers in step (iii) are subjected to a heat treatment at a temperature of 50° C. to 350° C.

14. The method according to claim 1, wherein the fibers in step (iii) are subjected to a heat treatment at a temperature of 80° C. to 280° C.

15. The method according to claim 1, wherein the fibers in step (iii) are subjected to a heat treatment at a temperature of 100° C. to 250° C.

16. The method according to claim 1, wherein the fibers in step (iii) are subjected to a heat treatment at a temperature of 140° C. to 220° C.

* * * * *